United States Patent [19]

Forsberg

[11] 3,968,791

[45] July 13, 1976

[54] ORTHOPEDIC BANDAGE COMPRISING DIACETONE ACRYLAMIDE, AND CAST PREPARED THEREFROM

[75] Inventor: John Wesley Forsberg, Mentor-on-the-Lake, Ohio

[73] Assignee: The Lubrizol Corporation, Cleveland, Ohio

[22] Filed: Jan. 29, 1975

[21] Appl. No.: 545,078

[52] U.S. Cl. ............................................. 128/90
[51] Int. Cl.² .......................................... A61F 5/04
[58] Field of Search ......................... 128/90, 89, 156

[56] References Cited
UNITED STATES PATENTS

| | | | |
|---|---|---|---|
| 3,604,413 | 9/1971 | Burg et al. | 128/90 |
| 3,656,476 | 4/1972 | Swinney | 128/90 |
| 3,669,708 | 6/1972 | Reber et al. | 128/90 X |
| 3,683,903 | 8/1972 | Fox et al. | 128/90 |
| 3,692,023 | 9/1972 | Phillips et al. | 128/90 |

Primary Examiner—John D. Yasko
Attorney, Agent, or Firm—James W. Adams, Jr.; William H. Pittman

[57] ABSTRACT

An orthopedic bandage for immobilizing or supporting portions of the body comprises a flexible carrier supporting a cast-forming composition comprising diacetone acrylamide and a water-insoluble condensation product of formaldehyde and diacetone acrylamide. The cast-forming composition may also contain fillers. The bandage is preferably prepared for use by dipping in water in the presence of a catalyst for initiating polymerization of the diacetone acrylamide and condensation product and then wrapping the body portion to be immobilized. The initiator may be a part of the bandage and may either be incorporated in the cast-forming composition or coated on the surface of the bandage.

9 Claims, No Drawings

ORTHOPEDIC BANDAGE COMPRISING DIACETONE ACRYLAMIDE, AND CAST PREPARED THEREFROM

This invention relates to orthopedic bandages used to form casts for immobilizing and supporting parts of the body such as fractured limbs to permit undisturbed healing. More specifically, it relates to an improved polymeric orthopedic bandage comprising a flexible carrier having adhered thereto a cast-forming composition comprising diacetone acrylamide and a water-insoluble condensation product of formaldehyde and diacetone acrylamide.

Plaster of Paris on fabric or gauze has been used almost exclusively in the preparation of surgical casts designed to immobilize and support portions of the body, e.g., a leg, arm, wrist, neck or the like. Plaster of Paris is inexpensive, convenient and ready to use after simply dipping in water. Moreover, practically all physicians, particularly orthopedic specialists, have long worked with plaster of Paris and are familiar with its application. Once having mastered the art of working with plaster of Paris, they are reluctant to learn the different techniques associated with other media.

Notwithstanding, plaster of Paris has certain shortcomings. It is relatively heavy and can be damaged by wetting with water. It is also substantially opaque to X-rays, thus sometimes requiring that a cast to be removed to ascertain, for example, whether a fracture has satisfactorily healed.

Past efforts to find substitutes for all or a portion of the plaster of Paris in orthopedic casts have been largely unsuccessful, in part because they required the mastering of new techniques and were less convenient to use and suffered from other shortcomings. For example, some substitute casts were substantially impervious to transmission of water vapor and thus perspiration. As another example, the use of thermoplastic sheets has been unacceptable because molding temperatures are too high. If an insulating medium is introduced between the thermoplastic material and the skin, the ability to mold or shape the thermoplastic material satisfactorily to the part to be immobilized is compromised.

Previous attempts to use resin structures have also proved largely unsuccessful. For example, the technique disclosed in U.S. Pat. No. 3,027,336 involves the application of a resin in the form of a paste which is inconvenient to prepare and represents a wide departure from the simple and convenient water-dipping technique associated with plaster of Paris. Moreover, it requires the presence of a poreforming agent to achieve porosity. Similarly, the technique of U.S. Pat. No. 3,089,486 involves the inconvenient impregnation of a polymer-imbued bandage with a liquid, curable monomer component immediately before or after the bandage is placed on the body member.

A principal object of the present invention, therefor, is to provide an orthopedic bandage which can be applied in substantially the same manner as plaster of Paris casts and yet avoids many of the disadvantages associated therewith.

A further object is to provide a plastic orthopedic cast which avoids many of the shortcomings of prior art plastic casts.

A further object is to provide an improved orthopedic bandage based on a polymerizable system which can be activated by simply immersing the same in an aqueous medium, at temperatures which are not excessive.

A further object is to provide a plastic-containing orthopedic cast which does not heat up excessively during curing.

Still another object is to provide a plastic component for orthopedic casts which is polymerizable under conditions normally encountered by physicians in applying plaster casts.

Other objects will in part be obvious and will in part appear hereinafter.

As previously noted, the orthopedic bandages of the present invention comprise a flexible carrier and a castforming composition adhered thereto. The flexible carrier may be any suitable support capable of carrying the castforming composition prior to polymerization thereof and otherwise compatible to its intended use. It should preferably be somewhat stretchable, conformable and inexpensive. In general, the same carriers employed in plaster of Paris casts may be used in the present invention.

Preferred carriers include open-mesh fabrics such as cotton gauze, cotton crinoline and other natural and synthetic bandage materials well known to those skilled in the art. For example, the carrier may be a cotton gauze having 10–50 warp and 10–50 weft threads to the square inch, some or all of the threads optionally being resilient or elastic.

The carrier may either be woven or non-woven and may also be manufactured in whole or part from plastic or glass fibers. The plastics may include, for example, polyethylene, polypropylene and various polyester or polyamide fibers, e.g., Dacron, nylon and the like. The carrier may also be prepared from porous foams such as polyester and polyether polyurethane foams. Other materials will be apparent to those skilled in the art in the light of the present disclosure.

The essential ingredients of the cast-forming composition, as previously noted, are diacetone acrylamide and a water-insoluble condensation product of formaldehyde and diacetone acrylamide. (For convenience herein, the combination of these two materials is sometimes referred to as the "resin system".) Both of these materials are known in the art. Diacetone acrylamide, i.e., N-(1,1-dimethyl-3 1-oxo-butyl)acrylamide, is disclosed in a large number of United States patents including U.S. Pat. No. 3,277,056. The water-insoluble diacetone acrylamide-formaldehyde condensation product, hereinafter sometimes referred to simply as the "condensation product," is disclosed in U.S. Pat. Re. No. 27,328. The reissue patent is incorporated by reference herein for its disclosure of the water-insoluble diacetone acrylamide-formaldehyde condensation product and its method of preparation.

The relative proportions of diacetone acrylamide and condensation product in the resin system may be varied within a wide range, depending on the properties desired in the orthopedic bandage. In general, high percentages of diacetone acrylamide tend to produce a crystalline consistency in the uncured bandage material, while high percentages of the condensation product tend to produce a resinous consistency therein. Resin systems containing about 10–90% (by weight) diacetone acrylamide, with the balance being condensation product, are especially contemplated, with mixtures containing 50–90% diacetone acrylamide being preferred.

The weight proportion of the resin system to the carrier may approximate the level employed in plaster of Paris orthopedic bandages. The amount of the resin system may be about 50–800% based on the weight of the support, and is typically about 200–500%. Techniques for controlling the proportions of the various ingredients of the bandage are discussed in U.S. Pat. No. 3,630,194, which is incorporated by reference herein for its disclosure of methods of making and working with orthopedic bandages of this type.

According to this invention, polymerization of the resin system and hardening of the bandage are catalyzed by a conventional redox initiator system. Suitable initiators are mixtures of oxidizing and reducing agents known to those skilled in the art, generally in proportions between about 1:9 and 9:1 by weight, preferably about 1:1. Said agents react substantially immediately with each other when dissolved in water. Accordingly, both cannot be mixed in aqueous solution until polymerization is to be initiated.

Examples of oxidizing agents are ammonium persulfate, potassium persulfate, hydrogen peroxide, t-butyl hydroperoxide, ferric chloride, hydroxylamine, cobalt (III) chloride, and potassium permanganate. Examples of reducing agents are ferrous sulfate, sodium sulfite, sodium dithionite, ferrous chloride, sodium formaldehyde sulfoxylate, oxalic acid, cobalt (II) chloride, and hydrazine. A catalyst concentration of about 0.5–5.0% by weight, based on water, is preferred although higher concentrations, e.g., about 5–10%, may be used.

Both the oxidizing and reducing agents are necessary for polymerization. Both initiators may be added to the water before the orthopedic bandage is dipped therein, or one of the two may be incorporated in the bandage at the time of its manufacture and the other added to the dipping water. Alternatively, catalytic amounts of both initiators may be incorporated in the bandage at the time of manufacture. Thus, the physician need only dip the bandage in water to prepare it for use. A specific example of a preferred catalyst system employed in this embodiment is ammonium persulfate and sodium sulfite. When both initiators are present, precautions should be taken to avoid contact with water or moisture-laden air prior to curing. As aqueous solutions of initiator tend to become acidic on standing, in the preferred practice a non-toxic, non-irritating buffer, such as sodium bicarbonate, sodium citrate, sodium acetate, disodium phosphate or the like, is added to avoid possible later irritation resulting from such acidification. Thus, a preferred accelerator is a three-part system containing, for example, potassium persulfate, sodium sulfite and sodium bicarbonate in approximately equal proportions by weight.

Other ingredients may be incorporated into the cast-forming composition, including binders, fillers, polymerization rate controllers, and the like. Thus, to bind the cast-forming composition to the carrier, and to prevent its loss upon contact with water to promote curing, a thin film of adhesive may be added to the ingredients at the time of manufacturing the bandage. Illustrative adhesives are latices such as Rhoplex B-15, a latex product of Rohm & Haas Company, and UCAR TCX-8960, a latex product of Union Carbide Corporation. Since contact with water in the presence of initiator prior to polymerization is undesirable, the water should be removed from a latex used as a binder system before the initiator is added.

Various types of fillers may be used, including polymeric fillers and water-insoluble inorganic salts. Fillers reduce the amount of resin system required. They also control the rate of water entering the bandage and thus the rate of reaction. By slowing the rate of reaction and increasing the bulk of the bandage, they reduce the temperature rise during polymerization and thus minimize discomfort to the patient.

Almost any non-toxic, non-irritating polymer can be used as a filler. Preferably, such polymer should coat out as a binder for the cast-forming composition. The binding action holds the composition on the carrier and minimizes undesired leaching into the dipping water. Examples of fillers are cellulose acetate, poly(methyl methacrylate), poly(diallyl phthalate), polycaprolactone, ethylene-maleic anhydride copolymers, styrene-maleic anhydride copolymers, poly(ethylene oxide), methylcellulose, carboxymethylcellulose, hydroxyethylcellulose and polyacrylamide.

Inorganic fillers may be added to improve the ease of wrapping of the bandage. In particular, they render the bandage less sticky and also moderate any temperature rise as noted above. Calcium sulfate or calcium carbonate are preferred, but other commercial fillers such as bentonite or silica can also be used.

When calcium sulfate hemihydrate, e.g., plaster of Paris, is employed as a filler, a hybrid system results. The resin system polymerizes and the plaster of Paris takes up water to form calcium sulfate dihydrate. Advantageously, neither the rate of polymerization of the resin system nor the hydration time of the plaster of Paris is unduly modified by the presence of the other reactive component.

Of the total solids in the cast-forming composition, the resin system comprises about 30–100% (by weight), with the balance being filler. The preferred ranges are about 50–80% resin system and about 20–50% other ingredients.

In the manufacture of the bandage of this invention, any suitable means may be used for applying the cast-forming composition to the carrier. Since the former is usually solid at room temperature, it is generally necessary to dissolve or disperse it in a suitable non-aqueous diluent (preferably a solvent) or to heat it above its melting point before coating it on the carrier. Coating may be by dipping, rolling, brushing, roller coating or the like.

When both initiators are incorporated in the cast-forming composition at the time of its manufacture, such composition and the orthopedic bandage containing the same must be maintained dry until the time of use, as previously discussed. Accordingly, in order to prevent premature polymerization the bandage is packaged, preferably in roll form, in a moisture-resistant container which is opened at the time of use.

Other details of manufacture of the orthopedic bandage of this invention will be found in the aforementioned U.S. Pat. No. 3,630,194.

The orthopedic bandage of this invention is prepared for use by contacting it with an aqueous medium, preferably water at about 110–140°F., preferably about 120–130°F., in the presence of catalytic amounts of a polymerization initiator. As described hereinabove, the initiator may be added to the aqueous medium or it may be incorporated in the cast-forming composition, or one ingredient of the two-component initiator may be incorporated in the cast-forming composition and the other added to the water at the time of dipping.

Following activation, the bandage is wrapped (usually in a plurality of layers) around the body member to be immobilized and the resin system polymerizes to form a rigid cast.

What is claimed is:

1. An orthopedic bandage comprising a flexible carrier having adhered thereto a cast-forming composition comprising diacetone acrylamide and a water-insoluble condensation product of formaldehyde and diacetone acrylamide.

2. An orthopedic bandage according to claim 1 wherein said cast-forming composition includes sufficient polymerization initiator to polymerize said diacetone acrylamide and condensation product in the presence of water.

3. An orthopedic bandage according to claim 2 wherein said polymerization initiator comprises a mixture of oxidizing and reducing agents.

4. An orthopedic bandage according to claim 2 wherein said polymerization initiator includes a buffer to control acidity.

5. An orthopedic bandage according to claim 4 wherein said polymerization initiator comprises a mixture of oxidizing and reducing agents.

6. An orthopedic bandage according to claim 1 wherein said cast-forming composition includes a solid filler.

7. A method of forming a rigid orthopedic cast for body members comprising the steps of immersing an orthopedic bandage according to claim 1 in an aqueous medium in the presence of a polymerization initiator, wrapping said orthopedic bandage around the body member to be immobilized, and allowing said diacetone acrylamide and condensation product to polymerize.

8. A method according to claim 7 wherein said polymerization initiator is present on said bandage prior to immersion thereof.

9. A rigid orthopedic cast prepared by the method of claim 7.

* * * * *